US 7,888,560 B1

(12) United States Patent
Cahoon et al.

(10) Patent No.: US 7,888,560 B1
(45) Date of Patent: Feb. 15, 2011

(54) PLANT TRANSCRIPTION FACTORS

(75) Inventors: Rebecca E. Cahoon, Wilmington, DE (US); Theodore M. Klein, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 467 days.

(21) Appl. No.: 11/899,370

(22) Filed: Sep. 4, 2007

Related U.S. Application Data

(63) Continuation of application No. PCT/US01/50908, filed on Oct. 24, 2001, now abandoned.

(60) Provisional application No. 60/242,739, filed on Oct. 24, 2000.

(51) Int. Cl.
*A01H 1/00* (2006.01)
*C07H 21/04* (2006.01)
*C12N 15/29* (2006.01)
*C07K 14/415* (2006.01)

(52) U.S. Cl. .................. 800/295; 435/6; 435/69.1; 435/468; 435/419; 435/320.1; 530/370; 536/23.6; 800/278; 554/227

(58) Field of Classification Search .............. 435/6, 435/69.1, 468, 419, 320.1; 536/23.2, 23.6, 536/24.1; 800/278, 295; 530/370
See application file for complete search history.

(56) References Cited

FOREIGN PATENT DOCUMENTS

| WO | WO 98/37184 | 8/1998 |
| WO | WO 99/67405 A2 | 12/1999 |
| WO | WO 00/28058 | 5/2000 |

OTHER PUBLICATIONS

Li et al., Nucleic Acids Research, vol. 20, 1992, pp. 1087-1091.*
Swall Database Accession No: Q9LF13, Oct. 1, 2000, H. Bloecker et al., XP002221974, Transcription Factor NF-Y, CCAAT-binding-like protein.
Tamar Lotan et al., Arabidopsis Leafy Cotyledon1 is Sufficient to Induce Embryo Development in Vegetative Cells, Cell, vol. 93:1195-1205, Jun. 26, 1998, XP-002136428.
EMBL Database Accession No: BE021941, Jun. 11, 2000, R. Shoemaker et al., Glycine max cDNA clone Genome Systems, XP-002221975.
National Center for Biotechnology Information General Identifier No. 22380, Accession No: CAA42234, Feb. 9, 1999, X. Y. Li et al., Evolutionary variation of the CCAAT-binding transcription factor NF-Y, Nucl. Acids Res., vol. 20(5):1087-1091, 1992.
National Center for Biotechnology Information General Identifier No. 2244810, Accession No: CAB10233, Jun. 29, 1999, M. Bevan et al.
National Center For Biotechnology Information General Identifier No. 2398529, Accession No: CAA74052, Sep. 12, 1997, D. Edwards et al., Isolation and characterisation of CCAAT box binding proteins from higher plants.
National Center for Biotechnology Information General Identifier No. 6729485, Accession No: CAB67641, Aug. 9, 2000, H. Bloecker et al.
National Center For Biotechnology Information General Identifier No. 3738293, Accession No: AAC63635, Mar. 11, 2002, S.D. Rounsley et al.
Xiao-Yan Li et al., Evolutionary variation of the CCAAT-binding transcription factor NF-Y, Nucleic Acids res., vol. 20(5):1087-1091, 1992.

* cited by examiner

*Primary Examiner*—Phuong T Bui

(57) ABSTRACT

This invention relates to an isolated nucleic acid fragment encoding a transcription factor. The invention also relates to the construction of a chimeric gene encoding all or a portion of the transcription factor, in sense or antisense orientation, wherein expression of the chimeric gene results in production of altered levels of accumulated oil in a transformed host cell.

9 Claims, 4 Drawing Sheets

```
SID  2: MAE------------------------APTSP----AGGSHESGGEQSPNTG--GVREQDRYLPIANISRIMKKALPANGKI
SID  4: MAE------------------------APASP---GGGGSHESGEHSPRSGG--AVREQDRYLPIANISRIMKKALPANGKI
SID  6: MAD------------------------D---------GGSHEGSG-GGGG-----VREQDRFLPIANISRIMKKAVPANGKI
SID  8: MPD----------------------------------SDNDSGG-PSN-AG-GELSS--PREQDRFLPIANVSRIMKKALPANAKI
SID 10: MPD----------------------------------SDNDSGG-PSNYAG-GELSS--PREQDRFLPIANISRIMKKALPANGKI
SID 12: MAD----------------------A-----------GHDESGSPPRSGG-----VREQDRFLPIANISRIMKKAVPANGKI
SID 14: MAE----------------------------------SDNDSGG-AQNAGNSGNLSELSPREQDRFLPIANVSRIMKKALPANAKI
SID 16: -TSSFWGISKSME------------DIGGSSNDNNNNGGII---------------KEQDRLLPIANVGRLMKRILPQNAKI
SID 18: MSD----------------------APASPCGGGGGSHESGEHSPRSN----FREQDRFLPIANISRIMKKALPPNGKI
SID 20: MAE----------------------------------SDNESGGHTGNASGSNELS--GCREQDRFLPIANVSRIMKKALPANAKI
SID 22: MAD----------------------GPASP---GGGSHESGDHSPRSN------VREQDRYLPIANISRIMKKALPANGKI
SID 24: MSD----------------------EAASPPGGGGGGGGGSDDGGGGGFGGVREQDRFLPIANISRIMKKAIPANGKI
SID 26: MPE----------------------------------SDNDSGG-PSNTGGEGELSS--PREQDRFLPIANVSRIMKKALPANAKI
SID 28: MAD----------------------------------DDSGSPRGGGG-------VREQDRFLPIANISRIMKKAVPANGKI
SID 30: MAE----------------------SGAP--------GTPESGHSGGGSGAREQDRCLPIANIGRIMRKAVPENGKI
SID 31: MAE----------------------SQTG---GGGG-GSHESGGDQSPRSL--NVREQDRFLPIANISRIMKRGLPLNGKI
SID 32: MA-----------------------EAPASPGGGGGSHESGSPRGGGGGG---SVREQDRFLPIANISRIMKKAIPANGKI
SID 33: M------------------------A-DSDN-DSGGHKDGGNAS--TREQDRFLPIANVSRIMKKALPANAKI
SID 34: R------------------------------------DRDSGG-GQNGNNQNGQSSLSPREQDRFLPIANVSRIMKKALPANAKI
SID 35: MAGNYHSFQNPIPRYQNYNFGSSSNHQHEHDGLVVVVEDQQQEESMVKEQDRLLPIANVGRIMKNILPANAKV
```

FIG. 1A

```
SID  2: AKDAKDTVQECVSEFISFITSEASDKCQKEKRKTINGDDLLWAMATLGFEDYIDPLKSYLTRYRELECDAKGSSR
SID  4: AKDAKETVQECVSEFISFITSEASDKCQREKRKTINGDDLLWPMATLGFEDYLDPLKIYLARYREMEGDTKGSAK
SID  6: AKDAKETLQECVSEFISFVTSEASDKCQKEKRKTINGDDLLWAMATLGFEEYVEPLKIYLQKYKEMEGDSKLSTK
SID  8: SKDAKETVQECVSEFISFITGEASDKCQREKRKTINGDDLLWAMTTLGFEDYVEPLKHYLHKFREIEGERAAASA
SID 10: SKDAKETVQECVSEFISFITGEASDKCQREKRKTINGDDLLWAMTTLGFEDYVDPLKHYLHKFREIEGERAAAST
SID 12: AKDAKETLQECVSEFISFVTSEASDKCQKEKRKTINGEDLLFAMGTLGFEEYVDPLKIYLHKYREMEGDSKLSSK
SID 14: SKDAKETVQECVSEFITGEASDKCQREKRKTINGDDLLWAMTTLGFEEYVEPLKIYLQRFREMEGEK------
SID 16: SKEAKETMQECVSEFISFVTSEASEKCRKERRKTVNGDDICWALATLGFDNYAEPMRRYLHRYREVDHNKVNL
SID 18: AKDAKETVQECVSEFISFVTSEASDKCQREKRKTINGDDLLWAMTTLGFEEYIDPLKVYLAAYREIEGDSKGSAK
SID 20: SKEAKETVQECVSEFISFITGEASDKCQKEKRKTINGDDLLWAMTTLGFEDYVDPLKIYLHKYREMEGEKTAM--
SID 22: AKDAKETVQECVSEFISFITSEL---CQREKRKTINGDDLLWAMATLGFEDYMDPLKIYLTRYREMEGDTKGSAK
SID 24: AKDAKETVQECVSEFISFITSEASDKCQREKRKTINGDDLLWAMATLGFEEYIEPLKVYLQKYRETEGDSKLAGK
SID 26: SKDAKETVOECVSEFISFITGEASDKCQREKRKTINGDDLLWAMTTLGFEDYVDPLKHYLHKFREIEGERAAATS
SID 28: AKDAKETLQECVSEFISFVTSEASDKCQKEKRKTINGDDLLWAMATLGFEEYVDPLKIYLQKYRDMEGDSKLTSK
SID 30: AKDAKESVQECVSEFISFVTSEASDKCRREKRKTINGDDLLWAMRMLGFEEYVEPLKLYLQLYREMEGNVMVS--
SID 31: AKDAKETMQECVSEFISFITGEASDKCQREKRKTINGDDLLWAMATLGFEDYIDPLKVYLMRYREMEGDTKGSGK
SID 32: AKDAKETMQECVSEFISFVTSEASDKCQREKRKTINGDDLLWAMATLGFEDYIEPLKVYLQKYREMEGDSKLTAK
SID 33: SKDAKETVQECVSEFISFITGEASDKCQREKRKTINGDDLLWAMTTLGFEDYVEPLKVYLQKYREVEGEK----
SID 34: SKDAKETMQECVSEFISFVTGEASDKCQKEKRKTINGDDLLWAMTTLGFEDYVEPLKVYLQRFREIEGER----
SID 35: SKEAKETMQECVSEFISFVTGEASDKCCHKEKRKTVNGDDICWAMANLGFDDYAAQLKKYLHRYRVLEGE--KPNH
```

FIG. 1B

```
SID  2: GGDESAK---RDAVGALPGQNS----QQYMQPG---AMTYINTQG----------------------QHLIIPSMQNNE-
SID  4: VGEASTK---RDGAAVQSVPNA----QIAHQSFSHGTNYSHSQV--------------------HHPALP-MHGSE-
SID  6: AGEGSVK---KDAISPHGGTSSSSNQ-LVQHGVYNQGMGYMQPQ-------------------------------
SID  8: -GASGSQQQQQGELPRGAANAAGYAGYAPGSG-GMMMMMGQPM-YGGSQPQQQPPPPQPPQQ-QQHQQHHM
SID 10: TGAGTSAASTTPPQQHTANAAGGYAGYAAPGAGPGGMMMMGQPM-YGS--------PPPPPQQ-QQQQHHHM
SID 12: AGDGSVK---KDTIGPHSGASSSSAQGMV--GAYTQGMGYMQPQ-------------------------------
SID 14: TVAAR-----DSSKDSASASS------------------------------------------YHQGHVY
SID 16: QEKGNSPEEKDDEL-------------------------------F----------------------------
SID 18: GGDASAK---RD----VYQSPNG----QVAHQGSFSQGVNYTNS------------------------------
SID 20: --MGRPHERDE-----------GYG--HGHGHATPMTMMMGH-------QPQHQ----HQH-QHQHQHQ-
SID 22: GGDSSAK---RD----VQPSPNA---QLAHQGSFSQNVTYPNSQG---------------RHMMVP-MQGPE-
SID 24: SGDVSVK---KDALGPHGGASGTSAQGMGQQVAYNPGMVYMQPQ------------------------------
SID 26: TSTAPQHLPDNN-----ATGYADYGGAAVPAPAPGGMMMM-GQPM-YGS--------PPP-----QQQHQHQV
SID 28: SGEGSVK---KDIIGAHSGATSSNAQAMVQHGAYAQGMGYMQPQ------------------------------
SID 30: --------------------------------------------------------------------------
SID 31: GGESSAK---RDGQPSQVSQFS----QVPQQGSFSQG-PYGNSQSLRFGNSIEHLEVLMSSTRTLFITIFRDSTM
SID 32: SSDGSIK---KDALG-HVGASSSAAEGMGQQGAYNQGMGYMQPQ------------------------------
SID 33: TT-----TAGRQGD--KEGGGGG-----GAGSGSGG-------------------------------------
SID 34: TGLGRPQTGGEVGEHQRDAVGDGG-----GFYGGGGM------------------------QYHQHHQF
SID 35: HGKGGPKSSPD------------------------------------------------------------
```

FIG. 1C

```
SID  2: ----------------------------------------
SID  4: ----------------------------------------
SID  6: ------------------YHN-----GET-----------
SID  8: AIGGRGGFGQQ---G-GGGGSSSSSGLGRQDR-A------
SID 10: AMGGRGGFGHHPGG-GGGGSSSSSGHGRQNRGA-------
SID 12: ------------------YHN-----GDT-----------
SID 14: ----GSPAYHHQ------VPGPTYPAP-----GRPR----
SID 16: ----------------KLSNRGVGL---------------
SID 18: ----------------------------------------
SID 20: ----GHVYG---------------SGSASSARTR------
SID 22: ----------------------------------------
SID 24: ------------------YHN-----GDISN---------
SID 26: AMGGRAGFPYHGGSSGGGGSSSSSGFGRKE---G------
SID 28: ------------------YHN-----GDT-----------
SID 30: --------------------------------------R
SID 31: PVVSENLSDPLSIDMDCEAIYHHF-IGLLILSCK------
SID 32: ------------------YHN-----GDIS-N--------
SID 33: ----APMYG----GGMVTTMGHQFS-------HHFS----
SID 34: LHQQNHMYGATGGGSDSGGGAASG--------RTRT----
SID 35: --------------------------------------N
```

FIG. 1D

SEQUENCE LISTING

<160> NUMBER OF SEQ ID NOS: 37

<210> SEQ ID NO 1
<211> LENGTH: 863
<212> TYPE: DNA
<213> ORGANISM: Momordica charantia

<400> SEQUENCE: 1

```
gcacgagcag gatctcgctc acatggcgga ggctccgacg agtccagccg gcggcagcca      60
cgagagcggc ggcgagcaga gccccaatac cggtggggtt cgggagcagg accgatacct     120
cccgatcgct aacattagcc ggatcatgaa gaaggccttg cccgctaatg caagatcgc      180
caaggacgcc aaggacaccg tccaggaatg cgtctccgaa ttcatcagct tcatcactag     240
cgaggcgagc gataagtgcc agaaggagaa gagaaagacc attaatgggg atgatttgct     300
gtgggcaatg gcgacattgg gtttcgagga ctatattgat ccgcttaagt cgtatctaac     360
taggtacaga gagttggagt gtgatgctaa gggatcttct aggggtggtg atgagtctgc     420
taaaagagat gcagttgggg ccttgcctgg ccaaaattcc cagcagtaca tgcagccggg     480
agcaatgacc tacattaaca cccaaggaca gcatttgatc attccttcaa tgcagaataa     540
tgaataggag actcctgcat tccctcttgg attgtctgaa atctgaggct ggtagaagcg     600
ttcaacacct atatagcatc tttacaatcg atttggctaa tttattatga aatgatgata     660
ttatatatat ttctggggtt tctgtgttgg ttctggattt gattttggtt tgggcttta      720
aggtgggctt cgattttatt gatgctctcg tcatctaaag ttattgtaaa tttgggacct     780
tcaatttagt atagttgctt tggtaatttg gaaactggaa aaaaaaaaa aaaaaaaaa       840
aaaaaaaaa aaaaaaaaa aaa                                               863
```

<210> SEQ ID NO 2
<211> LENGTH: 174
<212> TYPE: PRT
<213> ORGANISM: Momordica charantia

<400> SEQUENCE: 2

```
Met Ala Glu Ala Pro Thr Ser Pro Ala Gly Gly Ser His Glu Ser Gly
1               5                   10                  15

Gly Glu Gln Ser Pro Asn Thr Gly Gly Val Arg Glu Gln Asp Arg Tyr
            20                  25                  30

Leu Pro Ile Ala Asn Ile Ser Arg Ile Met Lys Lys Ala Leu Pro Ala
        35                  40                  45

Asn Gly Lys Ile Ala Lys Asp Ala Lys Asp Thr Val Gln Glu Cys Val
    50                  55                  60

Ser Glu Phe Ile Ser Phe Ile Thr Ser Glu Ala Ser Asp Lys Cys Gln
65                  70                  75                  80

Lys Glu Lys Arg Lys Thr Ile Asn Gly Asp Asp Leu Leu Trp Ala Met
                85                  90                  95

Ala Thr Leu Gly Phe Glu Asp Tyr Ile Asp Pro Leu Lys Ser Tyr Leu
            100                 105                 110

Thr Arg Tyr Arg Glu Leu Glu Cys Asp Ala Lys Gly Ser Ser Arg Gly
        115                 120                 125

Gly Asp Glu Ser Ala Lys Arg Asp Ala Val Gly Ala Leu Pro Gly Gln
    130                 135                 140
```

```
Asn Ser Gln Gln Tyr Met Gln Pro Gly Ala Met Thr Tyr Ile Asn Thr
145                 150                 155                 160

Gln Gly Gln His Leu Ile Ile Pro Ser Met Gln Asn Asn Glu
            165                 170

<210> SEQ ID NO 3
<211> LENGTH: 1179
<212> TYPE: DNA
<213> ORGANISM: Eucalyptus grandis

<400> SEQUENCE: 3
gcaccagttt cccccgccc ccccgatcgc cgcccctccc gccggggccg gcggcggcgg      60
ggcgtcggcg gcggcggcgg aggatgtggg gagctttctc acggaggatg aggtttcttc     120
tcttctatgt ttttttttt gcagctgctc ggcttgcctg ccctctcggg cgacgacgcg     180
atggcggagg ctccggcgag tcccggcggc ggcggcagcc acgagagcgg cgagcacagc     240
ccccggtccg gcggcgccgt ccgcgagcag gacaggtacc tccccatcgc caacatcagc     300
cgcatcatga agaaggccct ccccgccaac ggcaagatcg ccaaggacgc caaggagacc     360
gtgcaggagt gcgtctccga gttcatcagc ttcatcacca gcgaggcgag cgacaagtgc     420
cagagggaga agaggaagac gatcaacggc gacgacttgc tctggcccat ggcgacctta     480
gggtttgagg attacctcga tccgcttaag atttacctgg ccagatacag ggagatggag     540
ggggatacca aggggtcagc taaagtgggg gaagcatcta ctaaaagaga tggcgccgca     600
gttcagtcag ttcctaatgc acagattgct catcaaggtt cttctctca cggcaccaac      660 tattcgcatt ctcaagttca ccatcctgcg cttccgatgc atggctcaga atgacatgtt     720
ccagcccttg ttgcatgaga tgaagaagtc atcacacttg ttccaggcgt ttgactcatc     780
tcggcatcaa gatattcata agatgtgctg ctgacatttt agggtggtct ctgccaattg     840
tgttcatttg gagttgtttt ccagtgggct gtatatttta gcatctgcat catatttgct     900
ttcagcctta catatgtctg gtttagattt acttgataat gtagaaaggt aagcccccct     960
gcgagtattt atcttattgt catttagatt cgacacccaa ggaggacgag aatgaagttt    1020 cttttagct ctctgtttcg ttggagttgt cttgtgtatt cttgagttag aaacttgtga     1080
acaaattggt atgcacagtc catgtttatg tgacaatgtc gaggtctgag tgtataatcc    1140
agagtccaat tcagatcgta aaaaaaaaa aaaaaaaaa                            1179

<210> SEQ ID NO 4
<211> LENGTH: 177
<212> TYPE: PRT
<213> ORGANISM: Eucalyptus grandis

<400> SEQUENCE: 4

Met Ala Glu Ala Pro Ala Ser Pro Gly Gly Gly Gly Ser His Glu Ser
1               5                   10                  15

Gly Glu His Ser Pro Arg Ser Gly Gly Ala Val Arg Glu Gln Asp Arg
            20                  25                  30

Tyr Leu Pro Ile Ala Asn Ile Ser Arg Ile Met Lys Lys Ala Leu Pro
        35                  40                  45

Ala Asn Gly Lys Ile Ala Lys Asp Ala Lys Glu Thr Val Gln Glu Cys
    50                  55                  60

Val Ser Glu Phe Ile Ser Phe Ile Thr Ser Glu Ala Ser Asp Lys Cys
65                  70                  75                  80

Gln Arg Glu Lys Arg Lys Thr Ile Asn Gly Asp Asp Leu Leu Trp Pro
                85                  90                  95
```

Met Ala Thr Leu Gly Phe Glu Asp Tyr Leu Asp Pro Leu Lys Ile Tyr
            100                 105                 110

Leu Ala Arg Tyr Arg Glu Met Glu Gly Asp Thr Lys Gly Ser Ala Lys
        115                 120                 125

Val Gly Glu Ala Ser Thr Lys Arg Asp Gly Ala Ala Val Gln Ser Val
    130                 135                 140

Pro Asn Ala Gln Ile Ala His Gln Gly Ser Phe Ser His Gly Thr Asn
145                 150                 155                 160

Tyr Ser His Ser Gln Val His Pro Ala Leu Pro Met His Gly Ser
                165                 170                 175

Glu

<210> SEQ ID NO 5
<211> LENGTH: 983
<212> TYPE: DNA
<213> ORGANISM: Zea mays

<400> SEQUENCE: 5
gcacgagccg gagcgcctcc tcttctccag cgtccgatcc ccattcccca cctctcctcc      60
ctccgccgcc agctcccgcc cccttctctc cctcctcgc ctccccgcgc gcgcgttttt     120
ataagggttt cggcggaggc gcccggtcgc tggcgatggc cgacgacggc gggagccacg     180
agggcagcgg cggcggcgga ggcgtccggg agcaggaccg gttcctgccc atcgccaaca     240
tcagccggat catgaagaag gccgtcccgg ccaacggcaa gatcgccaag gacgctaagg     300
agaccctgca ggagtgcgtc tccgagttca tatcattcgt gaccagcgag gccagcgaca     360
aatgccagaa ggagaaacga agacaatca acggggacga tttgctctgg gcgatggcca     420
ctttaggatt cgaggagtac gtcgagcctc tcaagattta cctacaaaag tacaaagaga     480
tggagggtga tagcaagctg tctacaaagg ctggcgaggg ctctgtaaag aaggatgcaa     540
ttagtcccca tggtggcacc agtagctcaa gtaatcagtt ggttcagcat ggagtctaca     600
accaagggat gggctatatg cagccacagt accacaatgg ggaaacctaa taagggcta     660
atacagcagc aatttatgct agggaagtct ctgcattgct taccatgtgt attggcagaa     720
aacaggaggc acttacaaag ggtgttaatc tctgcgatgg ctgcctctca ggtgtaaatt     780
ggcttcggtt tagcgctgct tttgtccgta tatttaggat gatttgactg ttgctacttt     840
tggcaacctt ttacatttac agatatgtat tattcagcat aaatataata tagtagtcct     900
aggcctaaat aatggtgatt aacataccaa gtctttatc aggctactcg ttttctggaa     960
caaaaaaaaa aaaaaaaaaa aaa                                            983

<210> SEQ ID NO 6
<211> LENGTH: 164
<212> TYPE: PRT
<213> ORGANISM: Zea mays

<400> SEQUENCE: 6

Met Ala Asp Asp Gly Gly Ser His Glu Gly Ser Gly Gly Gly Gly Gly
1               5                   10                  15

Val Arg Glu Gln Asp Arg Phe Leu Pro Ile Ala Asn Ile Ser Arg Ile
            20                  25                  30

Met Lys Lys Ala Val Pro Ala Asn Gly Lys Ile Ala Lys Asp Ala Lys
        35                  40                  45

Glu Thr Leu Gln Glu Cys Val Ser Glu Phe Ile Ser Phe Val Thr Ser
    50                  55                  60

```
Glu Ala Ser Asp Lys Cys Gln Lys Glu Lys Arg Lys Thr Ile Asn Gly
65                  70                  75                  80

Asp Asp Leu Leu Trp Ala Met Ala Thr Leu Gly Phe Glu Glu Tyr Val
                85                  90                  95

Glu Pro Leu Lys Ile Tyr Leu Gln Lys Tyr Lys Glu Met Glu Gly Asp
            100                 105                 110

Ser Lys Leu Ser Thr Lys Ala Gly Glu Gly Ser Val Lys Lys Asp Ala
        115                 120                 125

Ile Ser Pro His Gly Gly Thr Ser Ser Ser Asn Gln Leu Val Gln
    130                 135                 140

His Gly Val Tyr Asn Gln Gly Met Gly Tyr Met Gln Pro Gln Tyr His
145                 150                 155                 160

Asn Gly Glu Thr

<210> SEQ ID NO 7
<211> LENGTH: 1021
<212> TYPE: DNA
<213> ORGANISM: Zea mays

<400> SEQUENCE: 7
ggcacgagcg ctcctgttct tctcgcatcc ccagcccagg tggtgtcccc tgtcgcgttg      60
atgcatgctc cctcggcggt ggccttgagc tgaggcggcg agcgatgcc ggactcggac      120 aacgactccg gcgggccgag caacgccggg ggcgagctgt cgtcgccgcg ggagcaggac      180
cggttcctgc ccatcgccaa cgtgagccgg atcatgaaga aggcgctccc ggccaacgcc      240
aagatcagca aggacgccaa ggagacggtg caggagtgcg tgtccgagtt catctccttc      300
atcaccggcg aggcctccga caagtgccag cgcgagaagc gcaagaccat caacggcgac      360
gacctgctgt gggccatgac cacgctcggc ttcgaggact acgtcgagcc gctcaagcac      420
tacctgcaca agttccgcga gatcgagggc gagagggccg ccgcgtccgc cggcgcctcg      480
ggctcgcagc agcagcagca gcagggcgag ctgcccagag gcgccgccaa tgccgccggg      540
tacgccgggt acggcgcgcc tggctccggc ggcatgatga tgatgatgat ggggcagccc      600
atgtacggcg gctcgcagcc gcagcaacag ccgccgccgc ctcagccgcc acagcagcag      660
cagcaacatc aacagcatca catggcaata ggaggcagag gaggattcgg ccaacaaggc      720
ggcggcggcg gctcctcgtc gtcgtcaggg cttggccggc aagacagggc gtgagttgcg      780
acgatacgtt cagaatcaga atcgctgata ctcctacgta gaattatacc tcctacctaa      840
ttgatgacac cgcaccgcac ctcgttgtgc tgcctgtcct tgtacgttta ctaattactg      900
ctgcctgtat gtaaatcaaa atctgaggct cccatttcga aacggacggt gaactactct      960
tcccgtttcg tttcatacga gaatcgaact cgttttcaat taaaaaaaaa aaaaaaaaa      1020 a                                                                      1021

<210> SEQ ID NO 8
<211> LENGTH: 222
<212> TYPE: PRT
<213> ORGANISM: Zea mays

<400> SEQUENCE: 8

Met Pro Asp Ser Asp Asn Asp Ser Gly Gly Pro Ser Asn Ala Gly Gly
1               5                   10                  15

Glu Leu Ser Ser Pro Arg Glu Gln Asp Arg Phe Leu Pro Ile Ala Asn
            20                  25                  30
```

-continued

Val Ser Arg Ile Met Lys Lys Ala Leu Pro Ala Asn Ala Lys Ile Ser
         35                  40                  45

Lys Asp Ala Lys Glu Thr Val Gln Glu Cys Val Ser Glu Phe Ile Ser
 50                  55                  60

Phe Ile Thr Gly Glu Ala Ser Asp Lys Cys Gln Arg Glu Lys Arg Lys
 65                  70                  75                  80

Thr Ile Asn Gly Asp Asp Leu Leu Trp Ala Met Thr Thr Leu Gly Phe
                 85                  90                  95

Glu Asp Tyr Val Glu Pro Leu Lys His Tyr Leu His Lys Phe Arg Glu
             100                 105                 110

Ile Glu Gly Glu Arg Ala Ala Ala Ser Ala Gly Ala Ser Gly Ser Gln
         115                 120                 125

Gln Gln Gln Gln Gly Glu Leu Pro Arg Gly Ala Ala Asn Ala Ala
     130                 135                 140

Gly Tyr Ala Gly Tyr Gly Ala Pro Gly Ser Gly Gly Met Met Met Met
145                 150                 155                 160

Met Met Gly Gln Pro Met Tyr Gly Ser Gln Pro Gln Gln Pro
                 165                 170                 175

Pro Pro Pro Gln Pro Pro Gln Gln Gln Gln His Gln His His
             180                 185                 190

Met Ala Ile Gly Gly Arg Gly Gly Phe Gly Gln Gly Gly Gly
         195                 200                 205

Gly Ser Ser Ser Ser Gly Leu Gly Arg Gln Asp Arg Ala
     210                 215                 220

<210> SEQ ID NO 9
<211> LENGTH: 1055
<212> TYPE: DNA
<213> ORGANISM: Oryza sativa

<400> SEQUENCE: 9
gcacgagctt acatctctct ctctcctctc ttctcttctt cctcccagac tagtcagtct      60
ctcccaagaa cacccactcc tctagtctct ctctcgagag agagaaaatt gatgattctt     120
gggatgattt tgaggcgtct gatttgctga agaggaggag gaggatgccg gactcggaca     180
acgactccgg cgggccgagc aactacgcgg aggggagct gtcgtcgccg cgggagcagg     240
acaggttcct gccgatcgcg aacgtgagca ggatcatgaa gaaggcgctg ccggcgaacg     300
ccaagatcag caaggacgcc aaggagacgg tgcaggagtg cgtctccgag ttcatctcct     360
tcatcaccgg cgaggcctcc gacaagtgcc agcgcgagaa gcgcaagacc atcaacggcg     420
acgacctgct ctgggccatg accaccctcg gcttcgagga ctacgtcgac cccctcaagc     480
actacctcca caagttccgc gagatcgagg gcgagcgcgc cgccgcctcc accaccggcg     540
ccggcaccag cgccgcctcc accacgccgc cgcagcagca gcacaccgcc aatgccgccg     600
gcggctacgc cgggtacgcc gccccgggag ccggccccgg cggcatgatg atgatgatgg     660
ggcagcccat gtacggctcg ccgccaccgc cgccacagca gcagcagcag caacaccacc     720
acatggcaat gggaggaaga ggcggcttcg gtcatcatcc cggcggcggc ggcggcgggt     780
cgtcgtcgtc gtcggggcac ggtcggcaaa acaggggcgc ttgacatcgc tccgagacga     840
gtagcatgca ccatggtaca tatatacagt aatcagcagc tgttcatttt tctatgatta     900
ctagttgact taagcttgca aatttgctaa tctgagctcc tgagtttttt ttttggtca     960
gcaatttcaa gatggtcaga agctaaattt gtctatttgt tactgataaa ttatttgttc    1020
tctcaaaaaa aaaaaaaaaa aaaaaaaaaa aaaaa                               1055

```
<210> SEQ ID NO 10
<211> LENGTH: 219
<212> TYPE: PRT
<213> ORGANISM: Oryza sativa

<400> SEQUENCE: 10

Met Pro Asp Ser Asp Asn Asp Ser Gly Gly Pro Ser Asn Tyr Ala Gly
1               5                   10                  15

Gly Glu Leu Ser Ser Pro Arg Glu Gln Asp Arg Phe Leu Pro Ile Ala
            20                  25                  30

Asn Val Ser Arg Ile Met Lys Lys Ala Leu Pro Ala Asn Ala Lys Ile
        35                  40                  45

Ser Lys Asp Ala Lys Glu Thr Val Gln Glu Cys Val Ser Glu Phe Ile
    50                  55                  60

Ser Phe Ile Thr Gly Glu Ala Ser Asp Lys Cys Gln Arg Glu Lys Arg
65                  70                  75                  80

Lys Thr Ile Asn Gly Asp Asp Leu Leu Trp Ala Met Thr Thr Leu Gly
                85                  90                  95

Phe Glu Asp Tyr Val Asp Pro Leu Lys His Tyr Leu His Lys Phe Arg
            100                 105                 110

Glu Ile Glu Gly Glu Arg Ala Ala Ala Ser Thr Thr Gly Ala Gly Thr
        115                 120                 125

Ser Ala Ala Ser Thr Thr Pro Pro Gln Gln Gln His Thr Ala Asn Ala
    130                 135                 140

Ala Gly Gly Tyr Ala Gly Tyr Ala Ala Pro Gly Ala Gly Pro Gly Gly
145                 150                 155                 160

Met Met Met Met Met Gly Gln Pro Met Tyr Gly Ser Pro Pro Pro
                165                 170                 175

Pro Gln Gln Gln Gln Gln His His His Met Ala Met Gly Gly Arg
            180                 185                 190

Gly Gly Phe Gly His His Pro Gly Gly Gly Gly Ser Ser Ser
        195                 200                 205

Ser Ser Gly His Gly Arg Gln Asn Arg Gly Ala
    210                 215

<210> SEQ ID NO 11
<211> LENGTH: 873
<212> TYPE: DNA
<213> ORGANISM: Oryza sativa

<400> SEQUENCE: 11 gttttttggag ggcggcgcgg ggatggcgga cgcggggcac gacgagagcg ggagcccgcc      60
gaggagcggc ggggtgaggg agcaggacag gttcctgccc atcgccaaca tcagccgcat     120
catgaagaag gccgtcccgg cgaacggcaa gatcgccaag gacgccaagg agaccctgca     180
ggagtgcgtc tcggagttca tctccttcgt caccagcgag gcgagcgaca aatgtcagaa     240
ggagaagcgc aagaccatca acggggaaga tctcctcttt gcgatgggta cgcttggctt     300
tgaggagtac gttgatccgt tgaagatcta tttacacaag tacagagaga tggagggtga     360
tagtaagctg tcctcaaagg ctggtgatgg ttcagtaaag aaggatacaa ttggtccgca     420
cagtggcgct agtagctcaa gtgcgcaagg gatggttggg gcttacaccc aagggatggg     480
ttatatgcaa cctcagtatc ataatgggga cacctaaaga tgaggacagt gaaaattttc     540
agtaactggt gtcctctgtg agttattatc catctgttaa ggaagaaccc acattagggc     600
catatttatt agtagaagac taaagcactt gaagggtgtt ggtttagaaa gggtgttaac     660
```

```
agttggctgt ggcgattgct tcacagatgt aaattgcttc ataagtggtt taatgcttgt    720
ttttgcctgt atattcagag caattttcac atattggtag ttctgcaatc ttttgcattc    780
ccatacatgt atcaggtggc acaaatctat tgcaagtacc ctagcattga ataatgctgg    840
ttaacatata aaaaaaaaaa aaaaaaaaaa aaa                                  873
```

<210> SEQ ID NO 12
<211> LENGTH: 164
<212> TYPE: PRT
<213> ORGANISM: Oryza sativa

<400> SEQUENCE: 12

```
Met Ala Asp Ala Gly His Asp Glu Ser Gly Ser Pro Pro Arg Ser Gly
1               5                   10                  15

Gly Val Arg Glu Gln Asp Arg Phe Leu Pro Ile Ala Asn Ile Ser Arg
            20                  25                  30

Ile Met Lys Lys Ala Val Pro Ala Asn Gly Lys Ile Ala Lys Asp Ala
        35                  40                  45

Lys Glu Thr Leu Gln Glu Cys Val Ser Glu Phe Ile Ser Phe Val Thr
    50                  55                  60

Ser Glu Ala Ser Asp Lys Cys Gln Lys Glu Lys Arg Lys Thr Ile Asn
65                  70                  75                  80

Gly Glu Asp Leu Leu Phe Ala Met Gly Thr Leu Gly Phe Glu Glu Tyr
                85                  90                  95

Val Asp Pro Leu Lys Ile Tyr Leu His Lys Tyr Arg Glu Met Glu Gly
            100                 105                 110

Asp Ser Lys Leu Ser Ser Lys Ala Gly Asp Gly Ser Val Lys Lys Asp
        115                 120                 125

Thr Ile Gly Pro His Ser Gly Ala Ser Ser Ser Ala Gln Gly Met
    130                 135                 140

Val Gly Ala Tyr Thr Gln Gly Met Gly Tyr Met Gln Pro Gln Tyr His
145                 150                 155                 160

Asn Gly Asp Thr
```

<210> SEQ ID NO 13
<211> LENGTH: 781
<212> TYPE: DNA
<213> ORGANISM: Glycine max

<400> SEQUENCE: 13

```
gcacgagacg aaagcaacgg tgaagatgaa taatgagtga ggcaatccaa tggtgagaaa     60
ggagtccgtg aaagcagaga cttatcgaga acaacggca cagaaggttc cacgtgggaa    120
gcagataaag gaatattaag cagagagatc caacggacac tgctagtgaa ggcagaagaa    180
gaagattcct ggattgattg tgaagatggc tgagtcggac aacgactcgg aggggcgca    240 gaacgcggga aacagtggaa acttgagcga gttgtcgcct cgggaacagg accggtttct    300
ccccatagcg aacgtgagca ggatcatgaa gaaggccttg ccggcgaacg cgaagatctc    360
gaaggacgcg aaggagacgg tgcaggaatg cgtgtcggag ttcatcagct tcataacggg    420
tgaggcgtcg acaagtgcc agagggagaa gcgcaagacc atcaacggcg acgatcttct    480
ctgggccatg acaaccctgg gattcgaaga gtacgtggag cctctgaaga tttacctcca    540
gcgcttccgc gagatggagg gagagaagac cgtggccgcc cgcgactctt ctaaggactc    600
ggcctccgcc tcctcctatc atcagggaca cgtgtacggc tccctgcct accatcatca    660 agtgcctggg cccacttatc ctgccctgg tagacccaga tgacgtgctc ctctattcgc    720
```

```
cactccctag acttttttata ttatattatt taattaaact ctcttctcca ctcaaccttt      780
g                                                                       781
```

<210> SEQ ID NO 14
<211> LENGTH: 165
<212> TYPE: PRT
<213> ORGANISM: Glycine max

<400> SEQUENCE: 14

```
Met Ala Glu Ser Asp Asn Asp Ser Gly Gly Ala Gln Asn Ala Gly Asn
1               5                   10                  15

Ser Gly Asn Leu Ser Glu Leu Ser Pro Arg Glu Gln Asp Arg Phe Leu
            20                  25                  30

Pro Ile Ala Asn Val Ser Arg Ile Met Lys Lys Ala Leu Pro Ala Asn
        35                  40                  45

Ala Lys Ile Ser Lys Asp Ala Lys Glu Thr Val Gln Glu Cys Val Ser
    50                  55                  60

Glu Phe Ile Ser Phe Ile Thr Gly Glu Ala Ser Asp Lys Cys Gln Arg
65                  70                  75                  80

Glu Lys Arg Lys Thr Ile Asn Gly Asp Asp Leu Leu Trp Ala Met Thr
                85                  90                  95

Thr Leu Gly Phe Glu Glu Tyr Val Glu Pro Leu Lys Ile Tyr Leu Gln
            100                 105                 110

Arg Phe Arg Glu Met Glu Gly Glu Lys Thr Val Ala Ala Arg Asp Ser
        115                 120                 125

Ser Lys Asp Ser Ala Ser Ala Ser Ser Tyr His Gln Gly His Val Tyr
    130                 135                 140

Gly Ser Pro Ala Tyr His His Gln Val Pro Gly Pro Thr Tyr Pro Ala
145                 150                 155                 160

Pro Gly Arg Pro Arg
                165
```

<210> SEQ ID NO 15
<211> LENGTH: 644
<212> TYPE: DNA
<213> ORGANISM: Glycine max

<400> SEQUENCE: 15

```
gcacgagcag tttctggggc atctcaaaat caatggaaga tattggaggc agttcctcaa       60
acgacaacaa caacaatggt ggcatcatca aggaacagga ccggttgctg ccaatagcca      120
atgttggtcg gctcatgaag cggattcttc ctcagaacgc caaaatctcg aaggaggcga      180
aggagacgat gcaggaatgt gtgtcggagt tcataagctt cgtgacgagt gaggcttcgg      240
agaagtgcag gaaggagagg aggaagacag tgaatggtga tgacatttgt tgggccttgg      300
caacactagg ctttgataac tatgctgaac caatgagaag gtacttgcat agatatagag      360
aggttgaggt agatcataat aaggtcaatc ttcaagaaaa agggaatagt cctgaagaga      420
aagacgatga attatttaaa ttgagcaata gaggggttgg gctttgacca attattatgc      480
ttatagtaga caggaactcg ttaatccatt catactcatc actgattact gattagatga      540
attagtaatt ttaaggtttt tgtgaggatg agataatata tgtaataatt ttcttgtctt      600
aattggaatt tatcgagctt agaacaaaaa aaaaaaaaaa aaaa                       644
```

```
<210> SEQ ID NO 16
<211> LENGTH: 152
<212> TYPE: PRT
<213> ORGANISM: Glycine max

<400> SEQUENCE: 16
```

Ser Phe Trp Gly Ile Ser Lys Ser Met Glu Asp Ile Gly Gly Ser Ser
1               5                   10                  15

Ser Asn Asp Asn Asn Asn Gly Gly Ile Ile Lys Glu Gln Asp Arg
            20                  25                  30

Leu Leu Pro Ile Ala Asn Val Gly Arg Leu Met Lys Arg Ile Leu Pro
            35                  40                  45

Gln Asn Ala Lys Ile Ser Lys Glu Ala Lys Glu Thr Met Gln Glu Cys
        50                  55                  60

Val Ser Glu Phe Ile Ser Phe Val Thr Ser Glu Ala Ser Glu Lys Cys
65                  70                  75                  80

Arg Lys Glu Arg Arg Lys Thr Val Asn Gly Asp Asp Ile Cys Trp Ala
                85                  90                  95

Leu Ala Thr Leu Gly Phe Asp Asn Tyr Ala Glu Pro Met Arg Arg Tyr
            100                 105                 110

Leu His Arg Tyr Arg Glu Val Glu Val Asp His Asn Lys Val Asn Leu
        115                 120                 125

Gln Glu Lys Gly Asn Ser Pro Glu Glu Lys Asp Glu Leu Phe Lys
    130                 135                 140

Leu Ser Asn Arg Gly Val Gly Leu
145                 150

```
<210> SEQ ID NO 17
<211> LENGTH: 879
<212> TYPE: DNA
<213> ORGANISM: Glycine max

<400> SEQUENCE: 17
gcacgagaag gaacgtgaaa gtaaaacgga cggtggcgat agaagcgtct ctcatctcca      60 tcgtcctc actcctctct tctccagcgt tcatttttc tcgcgcccaa atacaaaatc       120
acatcacaac agggttccgg cgaccatgtc cgatgctccg gcgagtccat gcggcggcgg     180
cggcggaggc agccacgaga gcggcgagca cagtccccgc tccaatttcc gcgagcagga     240
ccgcttcctc cccatcgcca acatcagccg catcatgaag aaagcgcttc ctcccaacgg     300
gaaaatcgcc aaggacgcca aggaaaccgt gcaggaatgc gtctccgagt tcatcagctt     360
cgtcaccagc gaagcgagcg ataagtgtca gagagagaag aggaagacca tcaacggcga    420
cgatttgctt tgggctatga ccactttagg tttcgaggag tatattgatc cgctcaaggt    480
ttacctcgcc gcttacagag agattgaggg tgattcaaag ggttcggcca agggtggaga   540
tgcatctgct aagagagatg tttatcagag tcctaatggc caggttgctc atcaaggttc    600
tttctcacaa ggtgttaatt atacgaattc ttagccccag gctcaacata tgatagttcc    660
gatgcaaggc caagagtaga tattgatcct ctccttcagt gtttgacatg tgtgatctaa    720
atgccagtgg aacttttatg tcaatatgtg cccttggtat aatgaatgca ttttatgtta    780
tgtaaacact acatgcgggg atgttggttc ttgtgaccag atattattta ttaagactta    840
catttatctt tggaaaaaaa aaaaaaaaa aaaaaaaa                              879
```

```
<210> SEQ ID NO 18
<211> LENGTH: 162
<212> TYPE: PRT
<213> ORGANISM: Glycine max

<400> SEQUENCE: 18

Met Ser Asp Ala Pro Ala Ser Pro Cys Gly Gly Gly Gly Gly Gly Ser
1               5                   10                  15

His Glu Ser Gly Glu His Ser Pro Arg Ser Asn Phe Arg Glu Gln Asp
            20                  25                  30

Arg Phe Leu Pro Ile Ala Asn Ile Ser Arg Ile Met Lys Lys Ala Leu
        35                  40                  45

Pro Pro Asn Gly Lys Ile Ala Lys Asp Ala Lys Glu Thr Val Gln Glu
    50                  55                  60

Cys Val Ser Glu Phe Ile Ser Phe Val Thr Ser Glu Ala Ser Asp Lys
65                  70                  75                  80

Cys Gln Arg Glu Lys Arg Lys Thr Ile Asn Gly Asp Asp Leu Leu Trp
                85                  90                  95

Ala Met Thr Thr Leu Gly Phe Glu Glu Tyr Ile Asp Pro Leu Lys Val
            100                 105                 110

Tyr Leu Ala Ala Tyr Arg Glu Ile Glu Gly Asp Ser Lys Gly Ser Ala
        115                 120                 125

Lys Gly Gly Asp Ala Ser Ala Lys Arg Asp Val Tyr Gln Ser Pro Asn
    130                 135                 140

Gly Gln Val Ala His Gln Gly Ser Phe Ser Gln Gly Val Asn Tyr Thr
145                 150                 155                 160

Asn Ser

<210> SEQ ID NO 19
<211> LENGTH: 771
<212> TYPE: DNA
<213> ORGANISM: Glycine max

<400> SEQUENCE: 19
gcacgagagt ctttagaaaa gatatccatg gctgagtccg acaacgagtc aggaggtcac      60
acggggaacg cgagcgggag caacgagttg tccggttgca gggagcaaga caggttcctc     120
ccaatagcaa acgtgagcag gatcatgaag aaggcgttgc cggcgaacgc gaagatatcg     180
aaggaggcga aggagacggt gcaggagtgc gtgtcggagt tcatcagctt cataacagga     240
gaggcttccg ataagtgcca aaggagaag aggaagacga tcaacggcga cgatcttctc     300
tgggccatga ctaccctggg cttcgaggac tacgtggatc ctctcaagat ttacctgcac     360
aagtataggg agatggaggg ggagaaaacc gctatgatgg aaggccaca tgagagggat     420 gagggttatg ccatggcca tggtcatgca actcctatga tgacgatgat gatggggcat     480
cagccccagc accagcacca gcaccagcac cagcaccagc accagggaca cgtgtatgga     540
tctggatcag catcttctgc aagaactaga tagcatgtgt catctgttta agcttaattg     600
attttattat gaggatgata tgatataaga tttatattcg tatatgtttg gttttagaaa     660
tacaccagct ccagcttgta attgcttgaa acttccttgt tgagagaata tagacattat     720
tgtggatggt gatgtggcaa aaaaaaaaaa aaaaaaaaaa aaaaaaaaa a                771

<210> SEQ ID NO 20
<211> LENGTH: 181
<212> TYPE: PRT
<213> ORGANISM: Glycine max
```

<400> SEQUENCE: 20

```
Met Ala Glu Ser Asp Asn Glu Ser Gly Gly His Thr Gly Asn Ala Ser
1               5                   10                  15

Gly Ser Asn Glu Leu Ser Gly Cys Arg Glu Gln Asp Arg Phe Leu Pro
            20                  25                  30

Ile Ala Asn Val Ser Arg Ile Met Lys Lys Ala Leu Pro Ala Asn Ala
        35                  40                  45

Lys Ile Ser Lys Glu Ala Lys Glu Thr Val Gln Glu Cys Val Ser Glu
    50                  55                  60

Phe Ile Ser Phe Ile Thr Gly Glu Ala Ser Asp Lys Cys Gln Lys Glu
65                  70                  75                  80

Lys Arg Lys Thr Ile Asn Gly Asp Asp Leu Trp Ala Met Thr Thr
            85                  90                  95

Leu Gly Phe Glu Asp Tyr Val Asp Pro Leu Lys Ile Tyr Leu His Lys
            100                 105                 110

Tyr Arg Glu Met Glu Gly Glu Lys Thr Ala Met Met Gly Arg Pro His
            115                 120                 125

Glu Arg Asp Glu Gly Tyr Gly His Gly His Gly His Ala Thr Pro Met
        130                 135                 140

Met Thr Met Met Met Gly His Gln Pro Gln His Gln His Gln His Gln
145                 150                 155                 160

His Gln His Gln His Gln Gly His Val Tyr Gly Ser Gly Ser Ala Ser
                165                 170                 175

Ser Ala Arg Thr Arg
            180
```

<210> SEQ ID NO 21
<211> LENGTH: 848
<212> TYPE: DNA
<213> ORGANISM: Glycine max

<400> SEQUENCE: 21

```
gcgccaaata caaattcgtg tcaacccaac ccagggttcc ggcgagcatg gccgacggtc      60
cggctagccc aggcggcggc agccacgaga gcggcgacca cagccctcgc tctaacgtgc     120
gcgagcagga caggtacctc cctatcgcta acataagccg catcatgaag aaggcacttc     180
ctgccaacgg taaaatcgca aggacgccaa agagaccgtt caggaatgc gtctccgagt      240
tcatcagctt catcaccagc gagttatgtc agagagaaaa gagaaagact attaacggcg     300
atgatttgct ctgggcgatg gccactctcg gtttcgagga ttatatggat cctcttaaaa     360
tttacctcac tagataccga gagatggagg gtgatacgaa gggctctgcc aagggtggag     420
actcatctgc taagagagat gttcagccaa gtcctaatgc tcagcttgct catcaaggtt     480
ctttctcaca aaatgttact tacccgaatt ctcagggtcg acatatgatg gttccaatgc     540
aaggcccgga gtaggtatca agtttattat tgaccctctt gttgtaacgt atgttttcta     600
cgccagttac caagtgctca cggcatattg aatgtctttt tatgttatgt gaatactgac     660
aggagatgtt ggttcttgtg tccgtttttt ttttttaaa ttaaggtttg tatattatct     720
ttggattcga attattattt gaaagttatt attatattgt aaatcctaga gccctgttgt     780
ctgaatccat caggcggctt ggtaaagacc gagattttag gactgattgt aagcataaat     840
ccgaatat                                                            848
```

<210> SEQ ID NO 22
<211> LENGTH: 168
<212> TYPE: PRT
<213> ORGANISM: Glycine max

<400> SEQUENCE: 22

```
Met Ala Asp Gly Pro Ala Ser Pro Gly Gly Ser His Glu Ser Gly
1               5                   10                  15

Asp His Ser Pro Arg Ser Asn Val Arg Glu Gln Asp Arg Tyr Leu Pro
                20                  25                  30

Ile Ala Asn Ile Ser Arg Ile Met Lys Lys Ala Leu Pro Ala Asn Gly
            35                  40                  45

Lys Ile Ala Lys Asp Ala Lys Glu Thr Val Gln Glu Cys Val Ser Glu
    50                  55                  60

Phe Ile Ser Phe Ile Thr Ser Glu Leu Cys Gln Arg Glu Lys Arg Lys
65                  70                  75                  80

Thr Ile Asn Gly Asp Asp Leu Leu Trp Ala Met Ala Thr Leu Gly Phe
                85                  90                  95

Glu Asp Tyr Met Asp Pro Leu Lys Ile Tyr Leu Thr Arg Tyr Arg Glu
                100                 105                 110

Met Glu Gly Asp Thr Lys Gly Ser Ala Lys Gly Gly Asp Ser Ser Ala
            115                 120                 125

Lys Arg Asp Val Gln Pro Ser Pro Asn Ala Gln Leu Ala His Gln Gly
    130                 135                 140

Ser Phe Ser Gln Asn Val Thr Tyr Pro Asn Ser Gln Gly Arg His Met
145                 150                 155                 160

Met Val Pro Met Gln Gly Pro Glu
                165
```

<210> SEQ ID NO 23
<211> LENGTH: 1091
<212> TYPE: DNA
<213> ORGANISM: Triticum aestivum

<400> SEQUENCE: 23

```
gcgccgcctt ctcttctcca gcgtcggatc ttcccccact cgccgccctc accgcacctc      60
cattcccctc caccaccttc cctccctcca cgcgctcctc tatataaggg ggagggccgg     120
atgtcggacg aggcggcgag ccccccgggc ggcggcggcg gcggaggagg cggcggcagc     180
gacgacggcg gcggcggcgg cggcttcggc ggcgtcaggg agcaggacag gttcctgccc     240
atcgccaaca tcagccgcat catgaagaag gccatcccgg ccaacggcaa gatcgccaag     300
gacgccaagg agaccgtgca ggagtgcgtc tccgagttca tctccttcat caccagcgag     360
gcgagcgaca agtgccagag ggagaagcgc aagaccatca acggcgacga cctgctctgg     420
gcgatggcca cgctgggctt cgaggagtac atcgagcccc tcaaggttta tctgcagaag     480
tacagagaga cggagggtga tagtaagcta gctgggaagt ctggtgatgt ctctgttaaa     540
aaggatgcac tgggtcctca tggaggagca agtggcacaa gtgcgcaagg gatgggccaa     600
caagtagcat acaatccagg aatggtttat atgcaacctc agtaccataa tggggacatc     660
tcaaactgaa gatatggacc atctccgaga ctgctgctac tctgctaggc gggttttcgt     720
catgtgagag cactaagca gttaaagaaa actcttagta cccccattag tctcgtgttg     780
ttgggtctgc agaactgat gctcaaaggc tgcttcccag atgtaaattg ctttttcctg     840
agaatagatt cagttgtggg ttagcatggt tgttgttgtt gtctgtatat ttatgatgat     900
tagcctcgtc gtggctgtca ttcggttcca tataatctgg gtatttgggg gagacataac     960
```

```
tcctccaagt gtaatttgtc ctggaactag ctgtttcaaa ctccttggaa gaagtgcttt      1020
taatccttca acagcgaagt caatcgtgtc acctcctgtc gggtgcaaca ttgctcctaa      1080
catgtataaa a                                                           1091
```

<210> SEQ ID NO 24
<211> LENGTH: 182
<212> TYPE: PRT
<213> ORGANISM: Triticum aestivum

<400> SEQUENCE: 24

```
Met Ser Asp Glu Ala Ala Ser Pro Pro Gly Gly Gly Gly Gly Gly Gly
1               5                   10                  15

Gly Gly Gly Ser Asp Gly Gly Gly Gly Gly Phe Gly Gly Val
            20                  25                  30

Arg Glu Gln Asp Arg Phe Leu Pro Ile Ala Asn Ile Ser Arg Ile Met
        35                  40                  45

Lys Lys Ala Ile Pro Ala Asn Gly Lys Ile Ala Lys Asp Ala Lys Glu
    50                  55                  60

Thr Val Gln Glu Cys Val Ser Glu Phe Ile Ser Phe Ile Thr Ser Glu
65                  70                  75                  80

Ala Ser Asp Lys Cys Gln Arg Glu Lys Arg Lys Thr Ile Asn Gly Asp
                85                  90                  95

Asp Leu Leu Trp Ala Met Ala Thr Leu Gly Phe Glu Glu Tyr Ile Glu
            100                 105                 110

Pro Leu Lys Val Tyr Leu Gln Lys Tyr Arg Glu Thr Glu Gly Asp Ser
        115                 120                 125

Lys Leu Ala Gly Lys Ser Gly Asp Val Ser Val Lys Lys Asp Ala Leu
    130                 135                 140

Gly Pro His Gly Gly Ala Ser Gly Thr Ser Ala Gln Gly Met Gly Gln
145                 150                 155                 160

Gln Val Ala Tyr Asn Pro Gly Met Val Tyr Met Gln Pro Gln Tyr His
                165                 170                 175

Asn Gly Asp Ile Ser Asn
            180
```

<210> SEQ ID NO 25
<211> LENGTH: 1016
<212> TYPE: DNA
<213> ORGANISM: Triticum aestivum

<400> SEQUENCE: 25

```
ctcgtgccgc aaagattgaa ttttcgtaca agtgtccttc cttccagtta acttcatgct       60
cctgcttgat caggctagag tggtttgatt gcttcttgat ttgagacaca gatcggggag      120
aggagccatg ccggagtcgg acaacgactc cggcgggccg agcaacaccg gcggggaggg      180
ggagctgtcg tcgccgcggg agcaggaccg cttcctgccc atcgccaacg tgagccgcat      240
catgaagaag gcgctcccgg ccaacgccaa gatcagcaag gacgccaagg agacggtgca      300
ggagtgcgtc tccgagttca tctccttcat caccggcgag gcctccgaca agtgccagcg      360
cgagaagcgc aagaccatca acggcgacga cctcctctgg gccatgacca ccctcggctt      420
cgaggactac gtcgaccccc tcaagcacta cctccacaag ttccgcgaga tcgagggcga      480
gagggccgcc gccacgtcga cgtcaaccgc gccgcagcac ctgcccgaca ataatgccac      540
cggttacgcc gactatggtg gcgccgctgt cccgcccccg gccccgggag gcatgatgat      600
gatggggcag cccatgtacg gctcaccgcc gccgcagcag cagcaccaac atcaggttgc      660
```

-continued

```
aatgggaggg agagcgggct ttccctatca cggaggcagc agcggtggcg gcgggtcgtc      720
ttcttcgtcg gggttcggac ggaaagaggg gtgacatctt ttcttttctt ttcgttttga      780
gctgaccaaa gtgagtgatt tcaacatatg ttcctctctt ggatgaagcc gtgacttgta      840 gcttaggga atccattcag tacaaggagg aataattgtt cagcaaatca gttttcttct      900
ataaacagga ggaatgtata actacgagtc tacaaatcat acctgggaag ctctccatga     960
attacttgtt taacaacatg gcgagacaca ataccaatat attgatgtta aaaaaa        1016
```

<210> SEQ ID NO 26
<211> LENGTH: 208
<212> TYPE: PRT
<213> ORGANISM: Triticum aestivum

<400> SEQUENCE: 26

```
Met Pro Glu Ser Asp Asn Asp Ser Gly Gly Pro Ser Asn Thr Gly Gly
 1               5                  10                  15

Glu Gly Glu Leu Ser Ser Pro Arg Glu Gln Asp Arg Phe Leu Pro Ile
             20                  25                  30

Ala Asn Val Ser Arg Ile Met Lys Lys Ala Leu Pro Ala Asn Ala Lys
         35                  40                  45

Ile Ser Lys Asp Ala Lys Glu Thr Val Gln Glu Cys Val Ser Glu Phe
     50                  55                  60

Ile Ser Phe Ile Thr Gly Glu Ala Ser Asp Lys Cys Gln Arg Glu Lys
 65                  70                  75                  80

Arg Lys Thr Ile Asn Gly Asp Asp Leu Leu Trp Ala Met Thr Thr Leu
                 85                  90                  95

Gly Phe Glu Asp Tyr Val Asp Pro Leu Lys His Tyr Leu His Lys Phe
            100                 105                 110

Arg Glu Ile Glu Gly Glu Arg Ala Ala Ala Thr Ser Thr Ser Thr Ala
        115                 120                 125

Pro Gln His Leu Pro Asp Asn Asn Ala Thr Gly Tyr Ala Asp Tyr Gly
    130                 135                 140

Gly Ala Ala Val Pro Ala Pro Ala Pro Gly Gly Met Met Met Met Gly
145                 150                 155                 160

Gln Pro Met Tyr Gly Ser Pro Pro Gln Gln Gln His Gln His Gln
                165                 170                 175

Val Ala Met Gly Gly Arg Ala Gly Phe Pro Tyr His Gly Gly Ser Ser
            180                 185                 190

Gly Gly Gly Gly Ser Ser Ser Ser Gly Phe Gly Arg Lys Glu Gly
        195                 200                 205
```

<210> SEQ ID NO 27
<211> LENGTH: 982
<212> TYPE: DNA
<213> ORGANISM: Triticum aestivum

<400> SEQUENCE: 27

```
gcacgaggca ttccccaccc ctcctcgcag cgccaaccac cgtctcctcc tcccccctcc      60
cttctctccc ctccgctcct cccccccgc gcgcgcgttt tttataaggg tttcggggcg     120
cgggatggcc gacgacgaca gcgggagccc ccggggcggc ggcggggtca gggagcagga     180
ccgcttcctc cccatcgcca acatcagccg catcatgaag aaggccgtgc cggccaacgg     240
caagatcgca aaggacgcca aggagaccct ccaggagtgc gtctccgagt tcatctcctt     300
cgtcaccagc gaggccagcg acaagtgcca gaaggagaag cgcaagacca tcaacgggga     360
```

-continued

```
cgatctgctc tgggccatgg ccacgctcgg attcgaggag tacgtagacc ccctcaagat    420
ctacctgcaa aagtacagag atatggaggg tgatagtaaa ttgacctcaa aatctggtga    480
aggatccgtg aagaaagata taattggtgc tcatagtggt gcgactagct caaacgccca    540
agcgatggtt cagcatggag cttacgccca agggatgggt tatatgcaac cccagtacca    600
taatggggac acctgaaact gaagatcagg caattttcgg caatgggtat tgctccatga    660
gtggttatct atctgttaag gaagccgccc aacattagg ttcatgatga tcattggctg    720
gaaactaaag cacctggaag ggtgcttaac agttggttgt gatggctgcc tccaagatgt    780
aaattgcttc cgagagaata gattcaccta ttatggttta gtgcttgttt ttatctgtac    840
attcagaata attcagccgt tggtagtttg gcaatctttt gtttcagata tttgtattag    900
gaagcataaa tatattacaa ctgggtatta acttataaaa aaaaaaaaa aaaaaaaaa    960 aaaaaaaaaa aaaaaaaaaa aa    982
```

<210> SEQ ID NO 28
<211> LENGTH: 163
<212> TYPE: PRT
<213> ORGANISM: Triticum aestivum

<400> SEQUENCE: 28

```
Met Ala Asp Asp Asp Ser Gly Ser Pro Arg Gly Gly Gly Val Arg
  1               5                  10                  15

Glu Gln Asp Arg Phe Leu Pro Ile Ala Asn Ile Ser Arg Ile Met Lys
                 20                  25                  30

Lys Ala Val Pro Ala Asn Gly Lys Ile Ala Lys Asp Ala Lys Glu Thr
             35                  40                  45

Leu Gln Glu Cys Val Ser Glu Phe Ile Ser Phe Val Thr Ser Glu Ala
         50                  55                  60

Ser Asp Lys Cys Gln Lys Glu Lys Arg Lys Thr Ile Asn Gly Asp Asp
     65                  70                  75                  80

Leu Leu Trp Ala Met Ala Thr Leu Gly Phe Glu Glu Tyr Val Asp Pro
                 85                  90                  95

Leu Lys Ile Tyr Leu Gln Lys Tyr Arg Asp Met Glu Gly Asp Ser Lys
            100                 105                 110

Leu Thr Ser Lys Ser Gly Glu Gly Ser Val Lys Lys Asp Ile Ile Gly
        115                 120                 125

Ala His Ser Gly Ala Thr Ser Ser Asn Ala Gln Ala Met Val Gln His
    130                 135                 140

Gly Ala Tyr Ala Gln Gly Met Gly Tyr Met Gln Pro Gln Tyr His Asn
145                 150                 155                 160

Gly Asp Thr
```

<210> SEQ ID NO 29
<211> LENGTH: 932
<212> TYPE: DNA
<213> ORGANISM: Canna edulis

<400> SEQUENCE: 29

```
gcaccagctc aaatctccga attagggttt ctgtgccttg tctccaatgg cggaatcggg     60
ggccccgggc acgcccgaga gcggacattc cggcggcgga tctggcgcgc gggagcagga    120
ccgctgcctc cccattgcca acattgggcg gattatgagg aaggccgtac ccgagaacgg    180
caagatcgcc aaggacgcca aggaatccgt ccaggagtgc gtctccgagt tcatcagctt    240
cgtcaccagc gaggcgagcg ataagtgccg ccgcgagaaa aggaagacga tcaacggcga    300
```

```
tgatcttctg tgggctatgc ggatgcttgg cttcgaagag tacgtcgagc ctcttaagct    360
ctacttgcag ctctacagag agatggaggg aaacgtcatg gtttcacgtc ccgctgatca    420
atgatcaacc aggaaaaaga gatggagcaa ttaacaggca gcccacagat tcgttcaatg    480
gcatgtagga tggttctcaa gaaagcaaac ttttgcttac tatttcaagg tgtaggccct    540
ttgttagtgt agttaataag ttatagttgc tgcaggttat ttttgttctt atttgtactc    600
ttgtccaata ccttttcctc taagtgaaca acattcagag aatggctctt ctctaggact    660
tggacgaagg cacgaagcac tgatctgaag ttatgatcca ttcaaccatc taaaattaat    720
tttaaatttt aaattgagac aatgtttga  cccttgtttc gacatttccc gacagcccta    780
ctgtaatgta aagatgactt ggatagcaaa attgttaaaa aggtacaatt cctgcaatgt    840
tttacaagtc aaaaaaaaaa aaaaaaaaaa aaaaaaaaaa aaaaaaaaaa aaaaaaaaaa    900
aaaaaaaaaa aaaaaaaaaa aaaaaaaaaa aa                                  932

<210> SEQ ID NO 30
<211> LENGTH: 125
<212> TYPE: PRT
<213> ORGANISM: Canna edulis

<400> SEQUENCE: 30

Met Ala Glu Ser Gly Ala Pro Gly Thr Pro Glu Ser Gly His Ser Gly
1               5                   10                  15

Gly Gly Ser Gly Ala Arg Glu Gln Asp Arg Cys Leu Pro Ile Ala Asn
            20                  25                  30

Ile Gly Arg Ile Met Arg Lys Ala Val Pro Glu Asn Gly Lys Ile Ala
        35                  40                  45

Lys Asp Ala Lys Glu Ser Val Gln Glu Cys Val Ser Glu Phe Ile Ser
    50                  55                  60

Phe Val Thr Ser Glu Ala Ser Asp Lys Cys Arg Arg Glu Lys Arg Lys
65                  70                  75                  80

Thr Ile Asn Gly Asp Asp Leu Leu Trp Ala Met Arg Met Leu Gly Phe
                85                  90                  95

Glu Glu Tyr Val Glu Pro Leu Lys Leu Tyr Leu Gln Leu Tyr Arg Glu
            100                 105                 110

Met Glu Gly Asn Val Met Val Ser Arg Pro Ala Asp Gln
        115                 120                 125

<210> SEQ ID NO 31
<211> LENGTH: 228
<212> TYPE: PRT
<213> ORGANISM: Arabidopsis thaliana

<400> SEQUENCE: 31

Met Ala Glu Ser Gln Thr Gly Gly Gly Gly Gly Ser His Glu Ser
1               5                   10                  15

Gly Gly Asp Gln Ser Pro Arg Ser Leu Asn Val Arg Glu Gln Asp Arg
            20                  25                  30

Phe Leu Pro Ile Ala Asn Ile Ser Arg Ile Met Lys Arg Gly Leu Pro
        35                  40                  45

Leu Asn Gly Lys Ile Ala Lys Asp Ala Lys Glu Thr Met Gln Glu Cys
    50                  55                  60

Val Ser Glu Phe Ile Ser Phe Val Thr Ser Glu Ala Ser Asp Lys Cys
65                  70                  75                  80

Gln Arg Glu Lys Arg Lys Thr Ile Asn Gly Asp Asp Leu Leu Trp Ala
                85                  90                  95
```

```
Met Ala Thr Leu Gly Phe Glu Asp Tyr Ile Asp Pro Leu Lys Val Tyr
            100                 105                 110

Leu Met Arg Tyr Arg Glu Met Glu Gly Asp Thr Lys Gly Ser Gly Lys
        115                 120                 125

Gly Gly Glu Ser Ser Ala Lys Arg Asp Gly Gln Pro Ser Gln Val Ser
    130                 135                 140

Gln Phe Ser Gln Val Pro Gln Gln Gly Ser Phe Ser Gln Gly Pro Tyr
145                 150                 155                 160

Gly Asn Ser Gln Ser Leu Arg Phe Gly Asn Ser Ile Glu His Leu Glu
                165                 170                 175

Val Leu Met Ser Ser Thr Arg Thr Leu Phe Ile Thr Ile Phe Arg Asp
            180                 185                 190

Ser Thr Met Pro Val Val Ser Glu Asn Leu Ser Asp Pro Leu Ser Ile
        195                 200                 205

Asp Met Asp Cys Glu Ala Ile Tyr His His Phe Ile Gly Leu Leu Ile
    210                 215                 220

Leu Ser Cys Lys
225

<210> SEQ ID NO 32
<211> LENGTH: 178
<212> TYPE: PRT
<213> ORGANISM: Zea mays

<400> SEQUENCE: 32

Met Ala Glu Ala Pro Ala Ser Pro Gly Gly Gly Gly Ser His Glu
1               5                   10                  15

Ser Gly Ser Pro Arg Gly Gly Gly Gly Gly Ser Val Arg Glu Gln
            20                  25                  30

Asp Arg Phe Leu Pro Ile Ala Asn Ile Ser Arg Ile Met Lys Lys Ala
        35                  40                  45

Ile Pro Ala Asn Gly Lys Ile Ala Lys Asp Ala Lys Glu Thr Val Gln
    50                  55                  60

Glu Cys Val Ser Glu Phe Ile Ser Phe Ile Thr Ser Glu Ala Ser Asp
65                  70                  75                  80

Lys Cys Gln Arg Glu Lys Arg Lys Thr Ile Asn Gly Asp Asp Leu Leu
                85                  90                  95

Trp Ala Met Ala Thr Leu Gly Phe Glu Asp Tyr Ile Glu Pro Leu Lys
            100                 105                 110

Val Tyr Leu Gln Lys Tyr Arg Glu Met Glu Gly Asp Ser Lys Leu Thr
        115                 120                 125

Ala Lys Ser Ser Asp Gly Ser Ile Lys Lys Asp Ala Leu Gly His Val
    130                 135                 140

Gly Ala Ser Ser Ser Ala Ala Glu Gly Met Gly Gln Gln Gly Ala Tyr
145                 150                 155                 160

Asn Gln Gly Met Gly Tyr Met Gln Pro Gln Tyr His Asn Gly Asp Ile
                165                 170                 175

Ser Asn

<210> SEQ ID NO 33
<211> LENGTH: 161
<212> TYPE: PRT
<213> ORGANISM: Arabidopsis thaliana
```

<400> SEQUENCE: 33

Met Ala Asp Ser Asp Asn Asp Ser Gly Gly His Lys Asp Gly Gly Asn
1               5                   10                  15

Ala Ser Thr Arg Glu Gln Asp Arg Phe Leu Pro Ile Ala Asn Val Ser
            20                  25                  30

Arg Ile Met Lys Lys Ala Leu Pro Ala Asn Ala Lys Ile Ser Lys Asp
        35                  40                  45

Ala Lys Glu Thr Val Gln Glu Cys Val Ser Glu Phe Ile Ser Phe Ile
    50                  55                  60

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
                85                  90                  95

Tyr Val Glu Pro Leu Lys Val Tyr Leu Gln Lys Tyr Arg Glu Val Glu
            100                 105                 110

Gly Glu Lys Thr Thr Ala Gly Arg Gln Gly Asp Lys Glu Gly Gly
        115                 120                 125

Gly Gly Gly Gly Ala Gly Ser Gly Ser Gly Ala Pro Met Tyr
    130                 135                 140

Gly Gly Gly Met Val Thr Thr Met Gly His Gln Phe Ser His His Phe
145                 150                 155                 160

Ser

<210> SEQ ID NO 34
<211> LENGTH: 187
<212> TYPE: PRT
<213> ORGANISM: Arabidopsis thaliana

<400> SEQUENCE: 34

Arg Asp Arg Asp Ser Gly Gly Gln Asn Gly Asn Asn Gln Asn Gly
1               5                   10                  15

Gln Ser Ser Leu Ser Pro Arg Glu Gln Asp Arg Phe Leu Pro Ile Ala
            20                  25                  30

Asn Val Ser Arg Ile Met Lys Lys Ala Leu Pro Ala Asn Ala Lys Ile
        35                  40                  45

Ser Lys Asp Ala Lys Glu Thr Met Gln Glu Cys Val Ser Glu Phe Ile
    50                  55                  60

Ser Phe Val Thr Gly Glu Ala Ser Asp Lys Cys Gln Lys Glu Lys Arg
65                  70                  75                  80

Lys Thr Ile Asn Gly Asp Asp Leu Leu Trp Ala Met Thr Thr Leu Gly
                85                  90                  95

Phe Glu Asp Tyr Val Glu Pro Leu Lys Val Tyr Leu Gln Arg Phe Arg
            100                 105                 110

Glu Ile Glu Gly Glu Arg Thr Gly Leu Gly Arg Pro Gln Thr Gly Gly
        115                 120                 125

Glu Val Gly Glu His Gln Arg Asp Ala Val Gly Asp Gly Gly Phe
    130                 135                 140

Tyr Gly Gly Gly Gly Met Gln Tyr His Gln His Gln Phe Leu
145                 150                 155                 160

His Gln Gln Asn His Met Tyr Gly Ala Thr Gly Gly Ser Asp Ser
                165                 170                 175

Gly Gly Gly Ala Ala Ser Gly Arg Thr Arg Thr
            180                 185

```
<210> SEQ ID NO 35
<211> LENGTH: 160
<212> TYPE: PRT
<213> ORGANISM: Arabidopsis thaliana

<400> SEQUENCE: 35

Met Ala Gly Asn Tyr His Ser Phe Gln Asn Pro Ile Pro Arg Tyr Gln
1               5                   10                  15

Asn Tyr Asn Phe Gly Ser Ser Ser Asn His Gln His Glu His Asp
            20                  25                  30

Gly Leu Val Val Val Glu Asp Gln Gln Gln Glu Glu Ser Met Met
        35                  40                  45

Val Lys Glu Gln Asp Arg Leu Leu Pro Ile Ala Asn Val Gly Arg Ile
 50                  55                  60

Met Lys Asn Ile Leu Pro Ala Asn Ala Lys Val Ser Lys Glu Ala Lys
 65                  70                  75                  80

Glu Thr Met Gln Glu Cys Val Ser Glu Phe Ile Ser Phe Val Thr Gly
                85                  90                  95

Glu Ala Ser Asp Lys Cys His Lys Glu Lys Arg Lys Thr Val Asn Gly
            100                 105                 110

Asp Asp Ile Cys Trp Ala Met Ala Asn Leu Gly Phe Asp Asp Tyr Ala
        115                 120                 125

Ala Gln Leu Lys Lys Tyr Leu His Arg Tyr Arg Val Leu Glu Gly Glu
    130                 135                 140

Lys Pro Asn His His Gly Lys Gly Gly Pro Lys Ser Ser Pro Asp Asn
145                 150                 155                 160

<210> SEQ ID NO 36
<211> LENGTH: 10
<212> TYPE: PRT
<213> ORGANISM: Artificial
<220> FEATURE:
<223> OTHER INFORMATION: Sequence element
<220> FEATURE:
<221> NAME/KEY: misc_feature
<222> LOCATION: (5)..(5)
<223> OTHER INFORMATION: Xaa can be any naturally occurring amino
      acid

<400> SEQUENCE: 36

Glu Gln Asp Arg Xaa Leu Pro Ile Ala Asn
1               5                   10

<210> SEQ ID NO 37
<211> LENGTH: 14
<212> TYPE: PRT
<213> ORGANISM: Artificial
<220> FEATURE:
<223> OTHER INFORMATION: Sequence element
<220> FEATURE:
<221> NAME/KEY: misc_feature
<222> LOCATION: (11)..(11)
<223> OTHER INFORMATION: Xaa can be any naturally occurring amino
      acid
<220> FEATURE:
<221> NAME/KEY: misc_feature
<222> LOCATION: (13)..(13)
<223> OTHER INFORMATION: Xaa can be any naturally occurring amino
      acid

<400> SEQUENCE: 37

Gln Glu Cys Val Ser Glu Phe Ile Ser Phe Xaa Thr Xaa Glu
1               5                   10
```

US 7,888,560 B1

PLANT TRANSCRIPTION FACTORS

This application is a continuation of the national stage entry of PCT/US01/50908 filed Oct. 24, 2001 and now abandoned, which claims the benefit of U.S. Provisional Application No. 60/242,739, filed Oct. 24, 2000, now expired, all of which are hereby incorporated by reference.

FIELD OF THE INVENTION

This invention is in the field of plant molecular biology. More specifically, this invention pertains to nucleic acid fragments encoding transcription factors in plants and seeds.

BACKGROUND OF THE INVENTION

Higher plant embryogenesis is divided conceptually into two distinct phases: early morphogenic processes that give rise to embryonic cell types, tissues, and organ systems, and late maturation events that allow the fully developed embryo to enter a desiccated and metabolically inactive state. Upon reception of the appropriate signals, the dormant embryo germinates, and seedling development begins. Thus, seed maturation and metabolic quiescence interrupt the morphogenetic processes that occur during embryogenesis and seedling development. This unique form of development underlies, in part, a plant's ability to make seeds, a trait that has conferred significant selective advantages to higher plants. Because lower plants do not make seeds and do not undergo embryo maturation, this bipartite mode of embryogenesis is thought to have resulted from the insertion of mutation events into the higher plant life cycle. Little is known at the mechanistic level about how distinct processes that occur during the morphogenesis and seed maturation phases are coordinated.

The leafy cotyledon) (LEC1) gene controls many distinct aspects of embryogenesis. The lec1 mutation is pleiotropic, which suggest that LEC1 has several roles in late embryo development. For example, LEC1 is required for specific aspects of seed maturation, inhibiting premature germination and plays a role in the specification of embryonic organ identity. Finally, LEC1 appears to act only during embryo development. Two other LEC class genes, LEC2 and FUSCA3 (FUS3), are thought to share similar or overlapping functions with LEC1, including the specification of cotyledon identity and the maintenance of maturation. It is unknown how LEC class genes act at the molecular level, but their involvement in many diverse aspects of embryogenesis suggests that these genes encode products that serve as regulators of higher plant embryonic processes. The LEC1-related transcription factors disclosed below all have homology to the maize CAAT-box DNA binding protein subunit B and the *Arabidopsis* LEC1 protein (WO 9837184-A) and as such may define a new family of LEC1 transcription factors.

Accordingly, the availability of nucleic acid sequences encoding all or a portion of these LEC1-related transcription factors would facilitate studies to better understand plant embryogenesis, and provide genetic tools for the manipulation of plant growth.

SUMMARY OF THE INVENTION

In a first embodiment, the present invention concerns an isolated polynucleotide comprising: (a) a nucleotide sequence encoding a polypeptide comprising at least 50 or 100 amino acids, wherein the amino acid sequence of the polypeptide and the amino acid sequence of OF SEQ ID NO:2, 4, 6, 8, 10, 12, 14, 16, 18, 20, 22, 24, 26, 28 or 30 have at least 90%, 91%, 92%, 93%, 94%, 95%, 96%, 97%, 98%, or 99% identity based on the Clustal alignment method, or (b) the complement of the nucleotide sequence, wherein the complement and the nucleotide sequence contain the same number of nucleotides and are 100% complementary. The polypeptide preferably comprises the amino acid sequence of OF SEQ ID NO:2, 4, 6, 8, 10, 12, 14, 16, 18, 20, 22, 24, 26, 28 or 30. The nucleotide sequence preferably comprises the nucleotide sequence of SEQ ID NO:1, 3, 5, 7, 9, 11, 13, 15, 17, 19, 21, 23, 25, 27, or 29. The polypeptide preferably is a Lec1-related transcription factor.

In a second embodiment, the present invention relates to a chimeric gene comprising any of the isolated polynucleotides of the present invention operably linked to a regulatory sequence, and a cell, a plant, and a seed comprising the chimeric gene.

In a third embodiment, the present invention relates to a vector comprising any of the isolated polynucleotides of the present invention.

In a fourth embodiment, the present invention relates to an isolated polynucleotide comprising a nucleotide sequence comprised by any of the polynucleotides of the first embodiment, wherein the nucleotide sequence contains at least 30, 40, or 60 nucleotides, and a cell, a plant, and a seed comprising the isolated polynucleotide.

In a fifth embodiment, the present invention relates to a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In a sixth embodiment, the present invention relates to a method for producing a transgenic plant comprising transforming a plant cell with any of the isolated polynucleotides of the present invention and regenerating a plant from the transformed plant cell, the transgenic plant produced by this method, and the seed obtained from this transgenic plant.

In a seventh embodiment, the present invention concerns an isolated polypeptide comprising an amino acid sequence comprising at least 50 or 100 amino acids, wherein the amino acid sequence and the amino acid sequence of OF SEQ ID NO:2, 4, 6, 8, 10, 12, 14, 16, 18, 20, 22, 24, 26, 28 or 30 have at least 90%, 91%, 92%, 93%, 94%, 95%, 96%, 97%, 98%, or 99% identity based on the Clustal alignment method. The amino acid sequence preferably comprises the amino acid sequence of OF SEQ ID NO:2, 4, 6, 8, 10, 12, 14, 16, 18, 20, 22, 24, 26, 28 or 30. The polypeptide preferably is a Lec1-related transcription factor.

In an eight embodiment, this invention relates to a method for isolating a polypeptide encoded by any of the polynucleotides of the first embodiment comprising transforming a cell with the polynucleotide, causing the polypeptide to be produced in the transformed cell, and isolating the polypeptide from the transformed cell.

In a ninth embodiment, the present invention relates to a virus, preferably a baculovirus, comprising any of the isolated polynucleotides of the present invention or any of the chimeric genes of the present invention.

In a tenth embodiment, the invention relates to a method of selecting an isolated polynucleotide that affects the level of expression of a gene encoding a Lec1-related transcription factor protein or activity in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the Lec1-related transcription factor protein or activity in the host cell containing the isolated polynucleotide; and (d) comparing the level of the Lec1-related transcription factor protein or activity in the host cell containing the isolated polynucleotide with the level of the Lec1-related transcription factor protein or activity in the host cell that does not contain the isolated polynucleotide.

In an eleventh embodiment, the invention concerns a method of obtaining a nucleic acid fragment encoding a substantial portion of a Lec1-related transcription factor protein, preferably a plant Lec1-related transcription factor protein comprising the steps of: synthesizing an oligonucleotide primer comprising a nucleotide sequence of at least one of 30 (preferably at least one of 40, most preferably at least one of 60) contiguous nucleotides derived from a nucleotide sequence selected from the group consisting of SEQ ID NOs: 3, 5, 7, 9, 11, 13, 15, 17, 19, 21, 23, 25, 27, and 29, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a Lec1-related transcription factor protein amino acid sequence.

In a twelfth embodiment, this invention relates to a method of obtaining a nucleic acid fragment encoding all or a substantial portion of the amino acid sequence encoding a Lec1-related transcription factor protein comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In a thirteenth embodiment, this invention concerns a method for positive selection of a transformed cell comprising: (a) transforming a host cell with the chimeric gene of the present invention or an expression cassette of the present invention; and (b) growing the transformed host cell, preferably a plant cell, such as a monocot or a dicot, under conditions which allow expression of the Lec1-related transcription factor polynucleotide in an amount sufficient to complement a null mutant to provide a positive selection means.

In a fourteenth embodiment, this invention relates to a method of altering the level of expression of a Lec1-related transcription factor protein in a host cell comprising: (a) transforming a host cell with a chimeric gene of the present invention; and (b) growing the transformed host cell under conditions that are suitable for expression of the chimeric gene wherein expression of the chimeric gene results in production of altered levels of the Lec1-related transcription factor protein in the transformed host cell.

BRIEF DESCRIPTION OF THE DRAWINGS AND SEQUENCE LISTINGS

The invention can be more fully understood from the following detailed description and the accompanying drawings and Sequence Listing that form a part of this application.

FIG. 1 shows a comparison of the amino acid sequences of the Lec1-related transcription factors from *Momordica* (SEQ ID NO:2, labeled SID2), eucalyptus (SID4), corn (SID 6 and 8), rice (SID 10 and 12), soybean (SID 14, 16, 18, 20, and 22), wheat (SID 24, 26, and 28), and *Canna* (SID30); compared to the closest prior art sequences from *Arabidopsis* (SID 31, 33, 34, and 35) and corn (SID32). Sequence elements EQDRXLPIAN (SEQ ID NO:36) and QECVSEFISFXTXE (SEQ ID NO:37), where "X" denotes any amino acid, are contained within the active site region of the polypeptide and appear to be characteristic of Lec1-related transcription factors.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821-1.825.

TABLE 1

LEC1-Related Transcription Factors

| Protein | Clone Designation | SEQ ID NO: (Nucleotide) | SEQ ID NO: (Amino Acid) |
|---|---|---|---|
| LEC-1-related transcription factor | fds.pk0003.h5 | 1 | 2 |
| LEC-1-related transcription factor | eef1c.pk004.c8 | 3 | 4 |
| LEC-1-related transcription factor | cbn10.pk0005.e6 | 5 | 6 |
| LEC-1-related transcription factor | p0006.cbysa51r | 7 | 8 |
| LEC-1-related transcription factor | r10n.pk0061.c8 | 9 | 10 |
| LEC-1-related transcription factor | rs11n.pk002.g10 | 11 | 12 |
| LEC-1-related transcription factor | ses4d.pk0037.e3 | 13 | 14 |
| LEC-1-related transcription factor | src2c.pk003.i13 | 15 | 16 |
| LEC-1-related transcription factor | src2c.pk011.m12 | 17 | 18 |
| LEC-1-related transcription factor | src2c.pk025.b3 | 19 | 20 |
| LEC-1-related transcription factor | src3c.pk028.j21 | 21 | 22 |
| LEC-1-related transcription factor | wkm1c.pk0002.d7 | 23 | 24 |
| LEC-1-related transcription factor | wlk8.pk0001.e10 | 25 | 26 |
| LEC-1-related transcription factor | wlm96.pk037.k9 | 27 | 28 |
| LEC-1-related transcription factor | ect1c.pk007.p18:fis | 29 | 30 |

The Sequence Listing contains the one letter code for nucleotide sequence characters and the three letter codes for amino acids as defined in conformity with the IUPAC-IUBMB standards described in *Nucleic Acids Res.* 93:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NO:1, 3, 5, 7, 9, 11, 13, 15, 17, 19, 21, 23, 25, 27, or 29, or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence selected from the group consisting of SEQ ID NO:1, 3, 5, 7, 9, 11, 13, 15, 17, 19, 21, 23, 25, 27, or 29, and the complement of such nucleotide sequences may be used to affect the expression and/or function of a LEC1-related transcription factor in a host cell. A method of using an isolated polynucleotide to affect the level of expression of a polypeptide in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic. Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5%

SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) J. Mol. Biol. 215:403-410; see also the explanation of the BLAST alogarithm on the world wide web site for the National Center for Biotechnology Information at the National Library of Medicine of the National Institutes of Health). In general, a sequence of ten or more contiguous amino acids or thirty or more contiguous nucleotides is necessary to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments that may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence that is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known, by those skilled in the art, as a technique that is used for the amplification of specific DNA segments (U.S. Pat. Nos. 4,683,195 and 4,800,159).

The present invention concerns an isolated polynucleotide comprising a nucleotide sequence encoding a LEC1-related transcription factor polypeptide having at least 90% identity, based on the Clustal method of alignment, when compared to a polypeptide selected from the group consisting of SEQ ID NO:2, 4, 6, 8, 10, 12, 14, 16, 18, 20, 22, 24, 26, 28 or 30.

This invention also relates to the isolated complement of such polynucleotides, wherein the complement and the polynucleotide consist of the same number of nucleotides, and the nucleotide sequences of the complement and the polynucleotide have 100% complementarity.

Nucleic acid fragments encoding at least a portion of several LEC1-related transcription factors have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other LEC1-related transcription factors, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably at least 40, most preferably at least 60) contiguous nucleotides derived from a nucleotide sequence selected from the group consisting of SEQ ID NO:1, 3, 5, 7, 9, 11, 13, 15, 17, 19, 21, 23, 25, 27, or 29 and the complement of such nucleotide sequences may be used in such methods to obtain a nucleic acid fragment encoding a substantial portion of an amino acid sequence of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

In another embodiment, this invention concerns viruses and host cells comprising either the chimeric genes of the invention as described herein or an isolated polynucleotide of the invention as described herein. Examples of host cells that can be used to practice the invention include, but are not limited to, yeast, bacteria, and plants.

As was noted above, the nucleic acid fragments of the instant invention may be used to create transgenic plants in which the disclosed polypeptides are present at higher levels when overexpressed, or lower levels when cosuppressed, than normal levels, or in cell types or developmental stages in which they are not normally found. This would have the effect of altering the level of gene expression for a LEC1-related transcription factor, which in turn would lead to altered expression of those genes controlled by the Lec1-related transcription factor. This would lead to developmental and phenotypic variations, such as but not limited to, over-accumulation of oils in tissues of the plant. For example, a seed specific promoter directing the overexpression of a Lec-1 related transcription factor will lead to the overexpression of oil in the seed.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations that may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one that allows large numbers of samples to be processed rapidly, since it will be expected that a large number of transformants will be negative for the desired phenotype.

In another embodiment, the present invention concerns a LEC1-related transcription factor polypeptide having an amino acid sequence that is at least 90% identical, based on the Clustal method of alignment, to a polypeptide selected from the group consisting of SEQ ID NO:2, 4, 6, 8, 10, 12, 14, 16, 18, 20, 22, 24, 26, 28 or 30.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded LEC 1-related transcription factor. An example of a vector for high level expression of the instant polypeptides in a bacterial host is provided (Example 7).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

Nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci. USA* 86:9402-9406; Koes et al. (1995) *Proc. Natl. Acad. Sci. USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from *Momordica charantia, Eucalyptus tereticornis*, corn, rice, soybean, wheat, and *Canna edulis* tissues were prepared. The characteristics of the libraries are described below.

TABLE 2 cDNA Libraries from *Momordica charantia, Eucalyptus tereticornis*, Corn, Rice, Soybean, Wheat, and *Canna edulis*

| Library | Tissue | Clone |
|---|---|---|
| fds | Momordica charantia developing seed | fds.pk0003.h5 |
| ect1c | *Canna edulis* tubers | ect1c.pk007.p18 |
| eef1c | *Eucalyptus tereticornis* flower buds from adult tree | eef1c.pk004.c8 |
| cbn10 | Corn developing kernel (embryo and endosperm); 10 days after pollination | cbn10.pk0005.e6 |
| p0006 | Corn young shoot | p0006.cbysa51r |
| r10n | Rice 15 day old leaf* | r10n.pk0061.c8 |
| rs11n | Rice 15-day-old seedling* | rs11n.pk002.g10 |
| ses4d | Soybean embryogenic suspension 4 days after subculture | ses4d.pk0037.e3 |
| src2c | Soybean 8 day old root infected with cyst nematode *Heterodera glycenis* | src2c.pk003.i13 src2c.pk011.m12 src2c.pk025.b3 |
| src3c | Soybean 8 day old root infected with cyst nematode *Heterodera glycenis* | src3c.pk028.j21 |
| wkm1c | Wheat kernel malted 55 hours at 22 degrees celsius | wkm1c.pk0002.d7 |
| wlk8 | Wheat seedlings 8 hours after treatment with herbicide** | wlk8.pk0001.e10 |
| wlm96 | Wheat seedlings 96 hours after inocidation with *Erysiphe graminis f. sp tritici* | wlm96.pk037.k9 |

*These libraries were normalized essentially as described in U.S. Pat. No. 5,482,845, incorporated herein by reference.
**Application of 6-iodo-2-propoxy-3-propyl-4(3H)-quinazolinone; synthesis and methods of using this compound are described in U.S. Ser. No. 08/545,827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors; plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences. (expressed sequence tags or "ESTs"; see Adams et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phred/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding LEC1-related transcription factors were identified by conducting BLAST (Basic Local Alignment Search Tool; Altschul et al. (1993) *J. Mol. Biol.* 215: 403-410; see also the explanation of the BLAST alogarithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389-3402) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches amino acid queries against a nucleotide database that is translated in all 6 reading frames. This search allows for differences in nucleotide codon usage between different species, and for codon degeneracy.

Example 3

Characterization of cDNA Clones Encoding LEC1-Related Transcription Factors

The BLASTX search using the EST sequences from clones listed in Table 3 revealed similarity of the polypeptides encoded by the cDNAs to LEC-1-related transcription factor from *Arabidopsis thaliana* (NCBI General Identifier No. gi 6729485), *Arabidopsis thaliana* (NCBI General Identifier No. gi 2398529), *Arabidopsis thaliana* (NCBI General Identifier No. gi 3738293), *Zea mays* (NCBI General Identifier No. gi 22380). Shown in Table 3 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 3

BLAST Results for Sequences Encoding Polypeptides Homologous to *Arabidopsis thaliana* and *Zea mays* LEC-1-Related Transcription Factors

| Clone | Status | BLAST pLog Score (NCBI General Identifier No.) |
|---|---|---|
| fds.pk0003.h5 | CGS | 57.70 (gi 6729485) |
| eef1c.pk004.c8 | CGS | 61.70 (gi 22380) |
| cbn10.pk0005.e6 | CGS | 72.22 (gi 22380) |
| p0006.cbysa51r | CGS | 55.52 (gi 2244810) |
| r10n.pk0061.c8 | CGS | 46.52 (22380) |
| rs11n.pk002.g10 | CGS | 68.70 (gi 22380) |
| ses4d.pk0037.e3 | CGS | 49.00 (gi 2398529) |
| src2c.pk003.i13 | CGS | 41.10 (gi 3738293) |
| src2c.pk011.m12 | CGS | 62.00 (gi 6729485) |
| src2c.pk025.b3 | CGS | 45.52 (gi 22380) |
| src3c.pk028.j21 | CGS | 54.30 (gi 22380) |
| wkm1c.pk0002.d7 | CGS | 79.52 (gi 22380) |
| w1k8.pk0001.e10 | CGS | 52.70 (gi 2398529) |
| w1m96.pk037.k9 | CGS | 73.52 (gi 22380) |
| ect1c.pk007.p18 | FIS | 44.70 (gi 22380) |

The sequence of the entire cDNA insert in the clones listed in Table 3 was determined. Further sequencing and searching of the DuPont proprietary database allowed the identification of other *Momordica, Eucalyptus, Canna*, corn, rice, soybean and/or wheat clones encoding Lec1-related transcription factors. The BLASTX search using the EST sequences from clones listed in Table 4 revealed similarity of the polypeptides encoded by the cDNAs to Lec1-related transcription factors from *Arabidopsis thaliana* (NCBI General Identifier No. 6729485, SEQ ID NO:31), *Zea mays* (NCBI General Identifier No. 22380, SEQ ID NO:32), *Arabidopsis thaliana* (NCBI General Identifier No. 2244810, SEQ ID NO:33), *Arabidopsis thaliana* (NCBI General Identifier No. 2398529, SEQ ID NO:34), *Arabidopsis thaliana* (NCBI General Identifier No. 3738293, SEQ ID NO:35). Shown in Table 4 are the BLAST results for individual ESTs ("EST"), sequences of the entire cDNA inserts comprising the indicated cDNA clones ("FIS"), sequences of contigs assembled from two or more ESTs ("Contig"), sequences of contigs assembled from an FIS and one or more ESTs ("Contig*"), or sequences derived from an FIS, a contig, or an FIS and PCR and encoding the entire protein ("CGS"):

TABLE 4

Percent Identity of Amino Acid Sequences Deduced From the Nucleotide Sequences of cDNA Clones Encoding Polypeptides Homologous to *Arabidopsis thaliana* and *Zea mays* LEC-1-Related Transcription Factors

| SEQ ID NO. | Percent Identity to (NCBI General Identifier No.) |
|---|---|
| 2 | 68% (gi 6729485) |
| 4 | 62% (gi 22380) |
| 6 | 80% (gi 22380) |
| 8 | 48% (gi 2244810) |
| 10 | 45% (gi 22380) |
| 12 | 81% (gi 22380) |
| 14 | 47% (gi 2398529) |
| 16 | 52% (gi 3738293) |
| 18 | 73% (gi 6729485) |
| 20 | 64% (gi 22380) |
| 22 | 62% (gi 22380) |
| 24 | 86% (gi 22380) |
| 26 | 54% (gi 2398529) |
| 28 | 77% (gi 22380) |
| 30 | 70% (gi 22380) |

Alignments of the disclosed sequences are shown in FIG. 1. A core region of approximately 90 amino acids is conserved in all of the polypeptides sequences. This region comprises a necessary functional domain for the transcription factor. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a LEC-1-related transcription factor. These sequences represent the first *Morordica, Eucalyptus*, rice, soybean and wheat and new corn sequences encoding LEC-1-related transcription factors known to Applicant.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform E. coli XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) Sci. Sin. Peking 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810-812) and the 3' region of the nopaline synthase gene from the T-DNA of the Ti plasmid of Agrobacterium tumefaciens.

The particle bombardment method (Klein et al. (1987) Nature 327:70-73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833-839).

Example 6

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) J. Biol. Chem. 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos that produce secondary embryos are then excised and placed into a suitable liquid medium. After repeated selection for clusters of somatic embryos that multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and Hind III sites was inserted at the BamHI site of pET-3a. This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into. DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide, wherein the polypeptide comprises the amino acid sequence of SEQ ID NO:6, or
   (b) the complement of the nucleotide sequence in (a), wherein the complement and the nucleotide sequence in (a) contain the same number of nucleotides and are 100% complementary;
   wherein a plant transformed with said isolated polynucleotide exhibits an over-accumulation of oils in tissues of the plant wherein the polynucleotide is expressed when compared to a plant that does not have said polynucleotide.

2. The polynucleotide of claim 1 wherein the nucleotide sequence comprises the nucleotide sequence of SEQ ID NO:5.

3. A vector comprising the polynucleotide of claim 1.

4. A recombinant DNA construct comprising the polynucleotide of claim 1 operably linked to a regulatory sequence.

5. A method for transforming a cell, comprising transforming a cell with the polynucleotide of claim 1.

6. A cell comprising the recombinant DNA construct of claim 4.

7. A method for producing a plant comprising transforming a plant cell with the polynucleotide of claim 1 and regenerating a plant from the transformed plant cell.

8. A plant comprising the recombinant DNA construct of claim 4.

9. A seed comprising the recombinant DNA construct of claim 4.

* * * * *